(12) United States Patent
Abarno

(10) Patent No.: US 7,264,469 B2
(45) Date of Patent: Sep. 4, 2007

(54) SPLIT-IMPLANT AND ABUTMENT SYSTEM FOR DENTAL RECONSTRUCTION

(75) Inventor: Juan Carlos Abarno, Av. Brasil 838, Salto, 50000 (UY)

(73) Assignee: Juan Carlos Abarno, Salto (UY)

( * ) Notice: Subject to any disclaimer, the term of this patent is extended or adjusted under 35 U.S.C. 154(b) by 244 days.

(21) Appl. No.: 11/122,857

(22) Filed: May 5, 2005

(65) Prior Publication Data

US 2005/0266381 A1    Dec. 1, 2005

Related U.S. Application Data

(63) Continuation-in-part of application No. 10/216,307, filed on Aug. 9, 2002.

(60) Provisional application No. 60/568,681, filed on May 7, 2004, provisional application No. 60/311,089, filed on Aug. 10, 2001.

(51) Int. Cl.
*A61C 8/00* (2006.01)

(52) U.S. Cl. ...................................................... 433/173

(58) Field of Classification Search ................. 433/173, 433/172, 174, 175, 176
See application file for complete search history.

(56) References Cited

U.S. PATENT DOCUMENTS

| | | | | |
|---|---|---|---|---|
| 4,086,701 A | | 5/1978 | Kawahara et al. | |
| 4,687,443 A | * | 8/1987 | Driskell | 433/173 |
| 5,810,592 A | | 9/1988 | Daftary | |
| 5,376,004 A | | 12/1994 | Mena | |
| 5,588,838 A | | 12/1996 | Hansson et al. | |
| 5,782,636 A | * | 7/1998 | Armstrong et al. | 433/165 |
| 5,863,200 A | | 1/1999 | Hamada et al. | |
| 5,915,967 A | * | 6/1999 | Clokie | 433/173 |
| 6,164,969 A | | 12/2000 | Dinkelacker | |
| 6,283,754 B1 | * | 9/2001 | Wohrle | 433/173 |
| 6,287,117 B1 | | 9/2001 | Niznick | |
| 6,375,465 B1 | * | 4/2002 | Engman et al. | 433/174 |
| 6,537,070 B1 | | 3/2003 | Stucki-McCormick | |
| 6,726,481 B1 | * | 4/2004 | Zickmann et al. | 433/173 |
| 6,743,018 B1 | | 6/2004 | Morrow | |
| 2001/0044095 A1 | | 11/2001 | Rizzo et al. | |
| 2003/0013068 A1 | | 1/2003 | Gittleman | |
| 2003/0031982 A1 | | 2/2003 | Abarno | |
| 2005/0100863 A1 | * | 5/2005 | Chang | 433/173 |

\* cited by examiner

*Primary Examiner*—Cary E. O'Connor
(74) *Attorney, Agent, or Firm*—Fay Sharpe Fagan Minnich & McKee; Brian E. Turung

(57) ABSTRACT

A dental implant assembly that includes an apical insert and at least one other component. The apical insert includes a top portion that is adapted to be at least partially secured to the component via a tapered Morse fit.

26 Claims, 16 Drawing Sheets

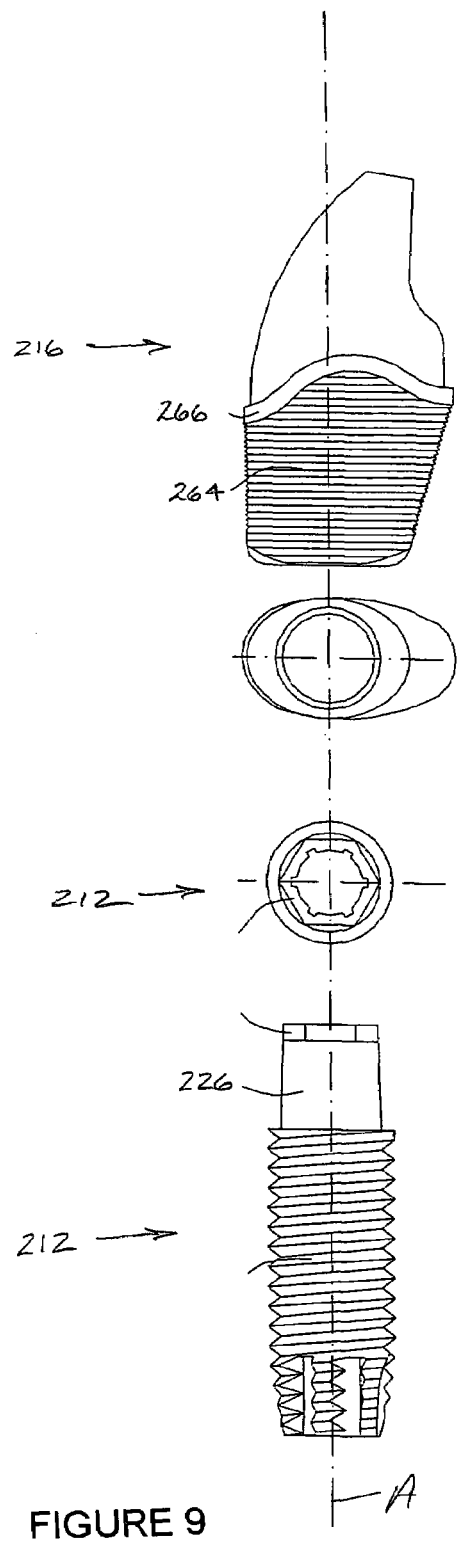
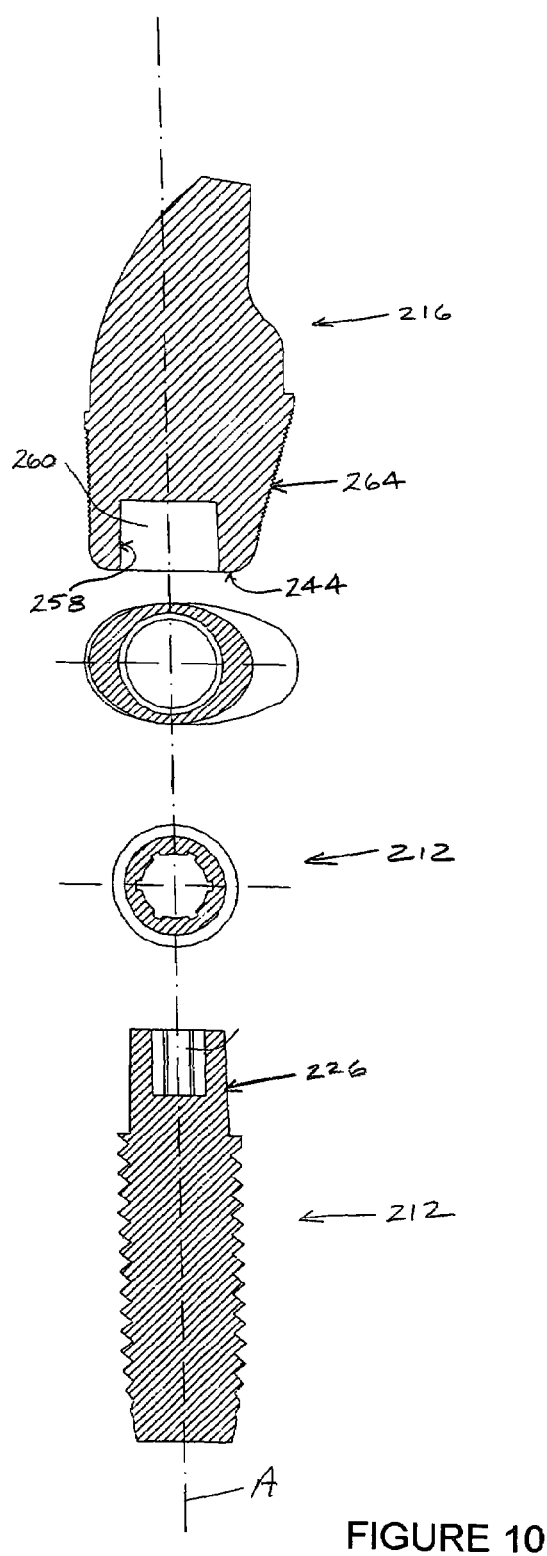
FIGURE 9
FIGURE 10

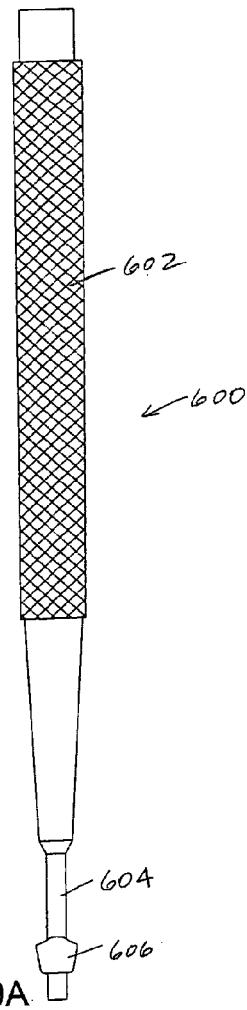
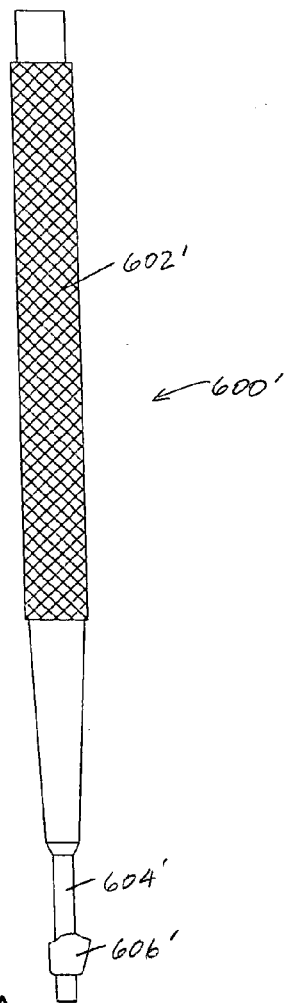
FIGURE 19A
FIGURE 20A
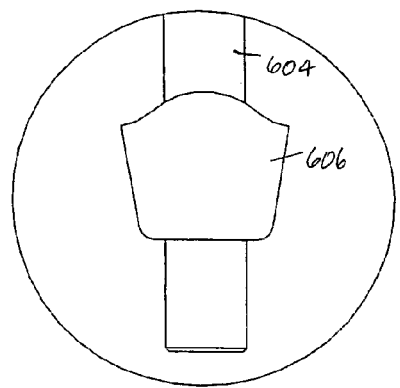
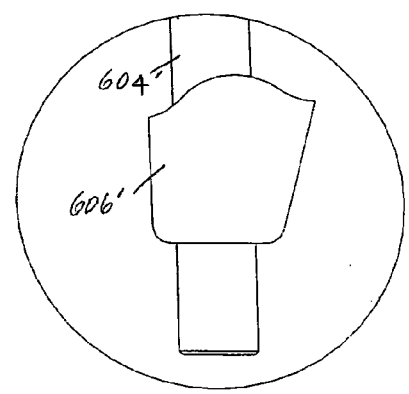
FIGURE 19B
FIGURE 20B

SPLIT-IMPLANT AND ABUTMENT SYSTEM FOR DENTAL RECONSTRUCTION

This application claims the benefit of U.S. Provisional Patent Application Ser. No. 60/568,681 which was filed on May 7, 2004 and is incorporated by reference.

This application is also a continuation-in-part of pending U.S. patent application Ser. No. 10/216,307 filed Aug. 9, 2002, pending, which claims priority to U.S. Application Ser. No. 60/311,089 filed Aug. 10, 2001.

The present invention is directed to implants and more particularly to an improved dental implant.

BACKGROUND OF THE INVENTION

Several dental implants are described in U.S. Pat. Nos. 6,743,018; 6,537,070; 6,287,117; 6,164,969; 5,810,592; 5,588,838; 5,376,004 and 4,086,701, and in a pending U.S. patent application Ser. No. 09/849,004 filed May 7, 2001 and Ser. No. 10/216,307 filed Aug. 9, 2002, all of which are incorporated by reference. There are several systems of dental implants in use today. Some of these systems try to resemble the anatomical root of a tooth. These systems, however, have at best produced marginal results. One problem associated with known dental implants is that they commonly include a circular cross section, while the tooth the implant intends to replace is not cylindrical, as illustrated in FIGS. 1A-1C.

This characteristic of conventional implants makes them unable to fully solve the problems that arise when the technique of extraction and immediate implant placement is used. As illustrated in FIG. 2, the circular fixture or platform PF of current implants does not completely fill the socket SK left by the removed tooth, thus a gap GP is left around the fixture. Such gaps extend in both labial and lingual directions due to the difference in shape between the circular fixture or platform PF and the oval or otherwise non-circular shaped socket SK remaining after the extraction of the tooth. This gap can result in undesired gaps between the dental implant and adjacent teeth, and/or can result in areas of food accumulation that can lead to gum and tooth disease.

Another disadvantage of known implants is that the resulting gap discussed above allows the socket to collapse after the tooth is extracted. As such, it is believed desirable to devise an implant that better reproduces the form of the extracted tooth so that the implant will largely fill the socket and such socket collapse can be minimized.

Another problem with known implants is that in situations in which there is less than 3 mm of separation between two adjacent implants, or between an implant and an adjacent tooth, resorption of the bone that separates these two items commonly takes place. Normally, the papilla found between the teeth and implants is supported by this bone. As a result, when the bone is resorbed, the height of the papilla is reduced, which may cause the subsequent collapse of the papilla altogether, which is, of course, undesirable and can impair the success of the dental implant. The circular platform of current implants commonly makes achieving the desired distance between an implant and an adjacent tooth or between two adjacent implants very difficult, if not impossible, as illustrated in FIG. 2 by dimensions A.

In many prior art dental implants, the platform upon which the prosthesis is to be mounted can extend through the emerging gingiva, which can be unattractive.

In view of the current state of technology relating to dental implants, there remains a need for a simple and effective dental implant that overcomes the various problems and deficiencies of past dental implants.

SUMMARY OF THE INVENTION

The present invention is directed to a dental implant that addresses many of the past problems associated with dental implants. In one embodiment of the present invention, the dental implant assembly includes an apical insert, a coronal base, an abutment, and a fastener. The apical insert is adapted to be inserted into an associated jaw bone. The apical insert includes a first portion having a generally conically shaped surface; however, it can be appreciated that other shapes can be used. The coronal base typically includes a threaded first cavity; however, this is not required. The coronal base includes an at least substantially conically shaped second cavity; however, it will be appreciated that other shapes can be used. The second cavity is dimensioned to receive the first portion of the apical insert such that the coronal base can mount to the apical insert. In one non-limiting arrangement, the apical insert is connected to the coronal base via a tapered Morse fit; however, it will be appreciated that other or additional connection arrangements can be used. The abutment typically includes a mounting passage. The fastener typically is a threaded fastener that extends through the mounting passage of the abutment and threadingly engages the coronal base in the first cavity. As can be appreciated the fastener does not have to include a thread and/or can include other arraignments to engage the coronal base.

In another and/or alternative embodiment of the present invention, the dental implant assembly includes an apical insert and an abutment. The apical insert is adapted to be inserted into an associated jawbone. The apical insert includes a first portion having an at least substantially conically shaped external surface; however, it can be appreciated that other shapes can be used. The abutment is adapted to support an associated dental prosthesis. The abutment includes an at least substantially conically shaped cavity surface; however, it can be appreciated that other shapes can be used. The cavity surface is dimensioned to receive the first portion of the apical insert such that the abutment can mount to the apical insert. In one non-limiting arrangement, the apical insert is connected to the coronal base via a tapered Morse fit; however, it will be appreciated that other or additional connection arrangements can be used.

In still another and/or alternative embodiment of the present invention, there is provided a method for inserting a dental implant assembly of the present invention into a patient's jawbone. This method includes the steps of inserting an apical insert into a patient's jawbone and mounting a component selected from the group comprising a coronal base and an abutment to the apical insert. The apical insert includes a first portion having an at least substantially conically shaped external surface; however, it can be appreciated that other shapes can be used. The apical insert is typically inserted fully in the jawbone such that the top portion of the apical insert is flush with or below the top surface of the jawbone. In one non-limiting arrangement, the apical insert is embedded in the jaw bone such that the top surface is positioned below the top surface of the jawbone. In this arrangement, the component that is positioned and connected to the top of the apical insert is also at least partially embedded in the jaw bone. The component includes an at least substantially conically shaped cavity; however, it can be appreciated that other shapes can be used. The cavity surface is dimensioned to receive the first portion of the apical insert such that the abutment can mount to the apical insert. In one non-limiting arrangement, the apical insert is connected to the coronal base via a tapered Morse fit; however, it will be appreciated that other or additional connection arrangements can be used.

These and other advantages will become apparent from the following description taken together with the accompanying drawing.

BRIEF DESCRIPTION OF THE DRAWINGS

Reference may now be made to the drawings, which illustrate various embodiments that the invention may take in physical form and in certain parts and arrangements of parts wherein;

FIG. 9 is an exploded view of another embodiment of a dental implant assembly also including a top plan view of an apical insert of the assembly and a bottom plan view of an abutment of the assembly;

FIG. 10 is an exploded, cross-sectional view of the assembly shown in FIG. 9;

FIG. 19A is a side view of an osteotome for preparing an implantation site to receive a dental implant assembly;

FIG. 19B is a close-up view of a lower portion of the osteotome of FIG. 19A;

FIG. 20A is a side view of another embodiment of an osteotome for preparing an implantation site to receive a dental implant assembly;

FIG. 20B is a close-up view of a lower portion of the osteotome of FIG. 20A;

DETAILED DESCRIPTION

Figure 1A:
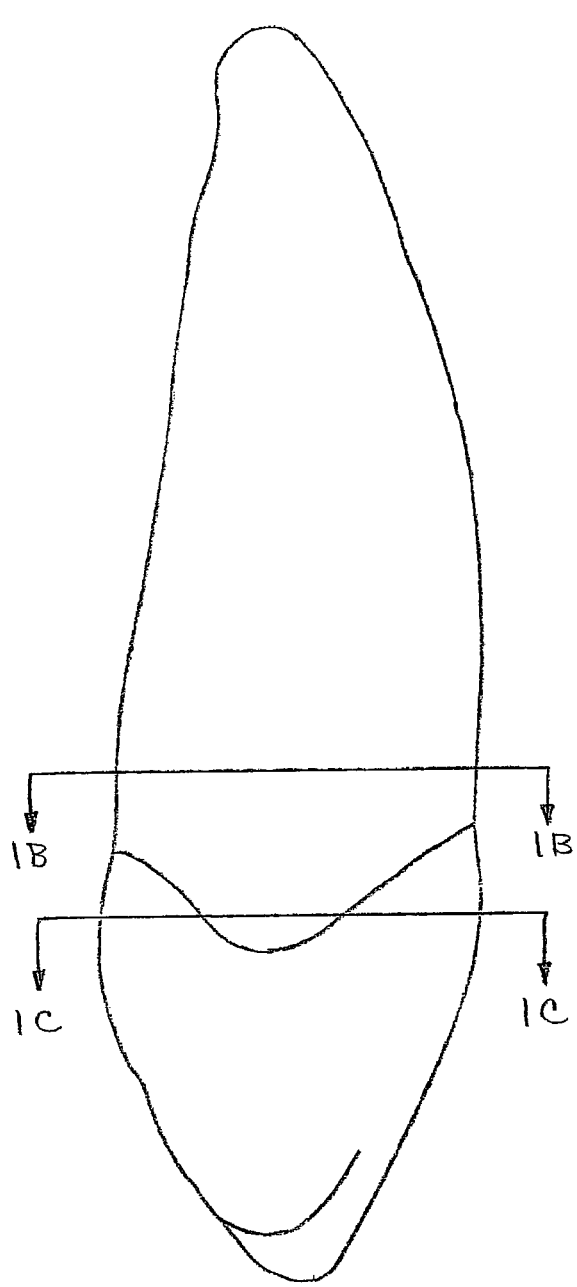
FIG. 1A is a side view of a tooth shown having varying cross sections.
Figure 1B:
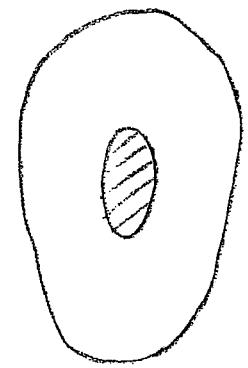
FIG. 1B is a cross-sectional view taken at line 5 of FIG. 1A.
Figure 1C:
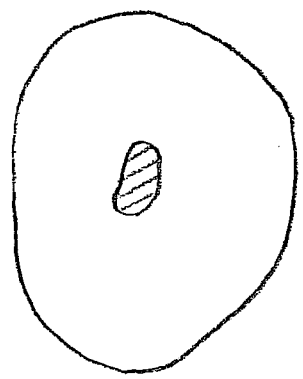
FIG. 1C is a cross-sectional view taken at line 4 of FIG. 1A.
Figure 2:
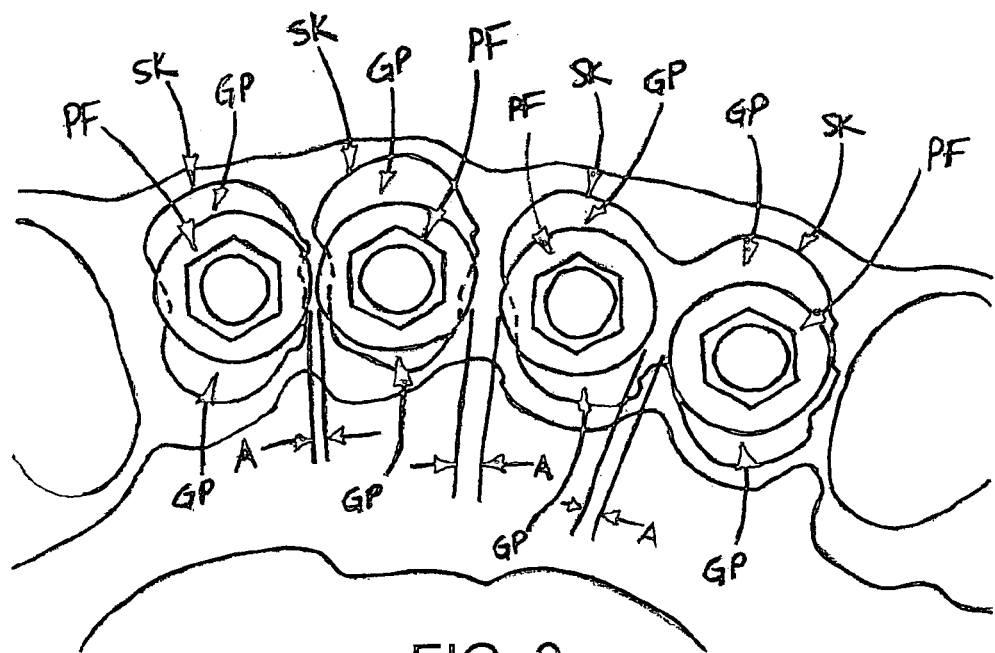
FIG. 2 is an illustration of prior art dental implants shown superimposed over a section of jawbone having sockets left by removed teeth.
Figure 3:
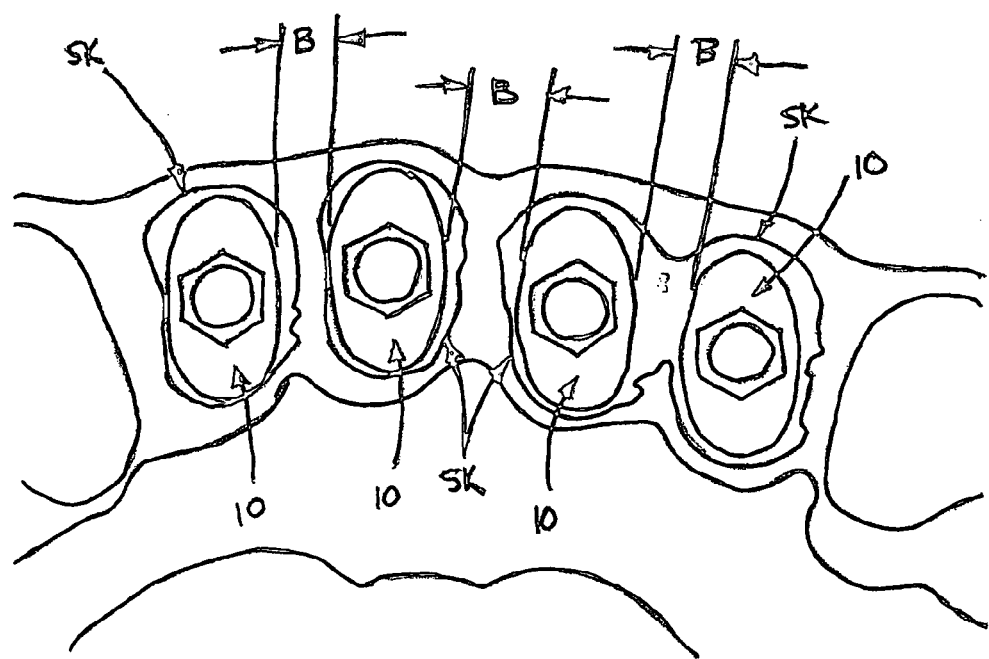
FIG. 3 is an illustration of dental implants in accordance with an embodiment of the present invention shown superimposed over a section of jawbone having sockets left by removed teeth.
Figure 4:
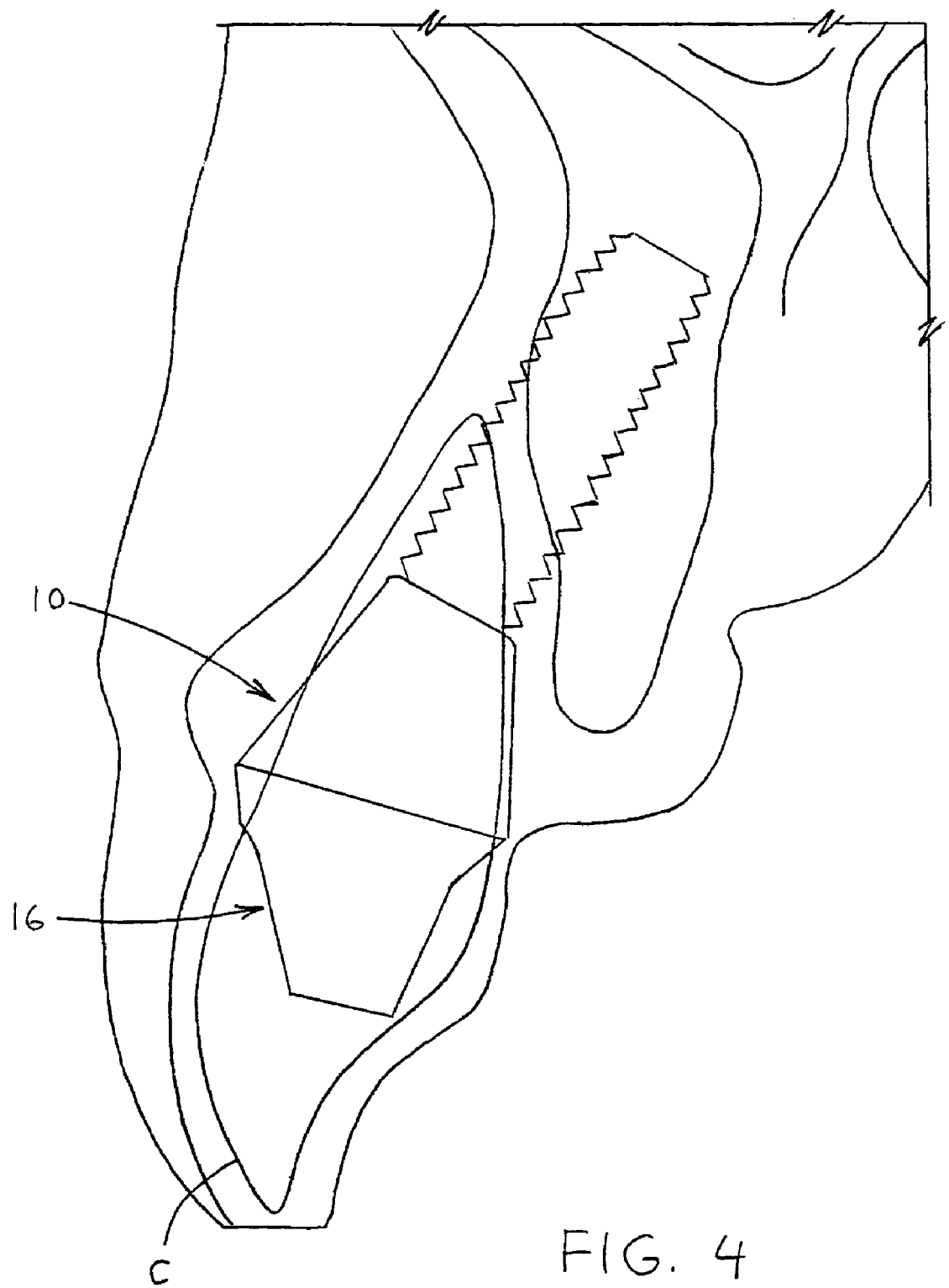
FIG. 4 illustrates a dental implant assembly in accordance with an embodiment of the present invention shown superimposed over a section of jawbone and a tooth.
Figures 5, 6:
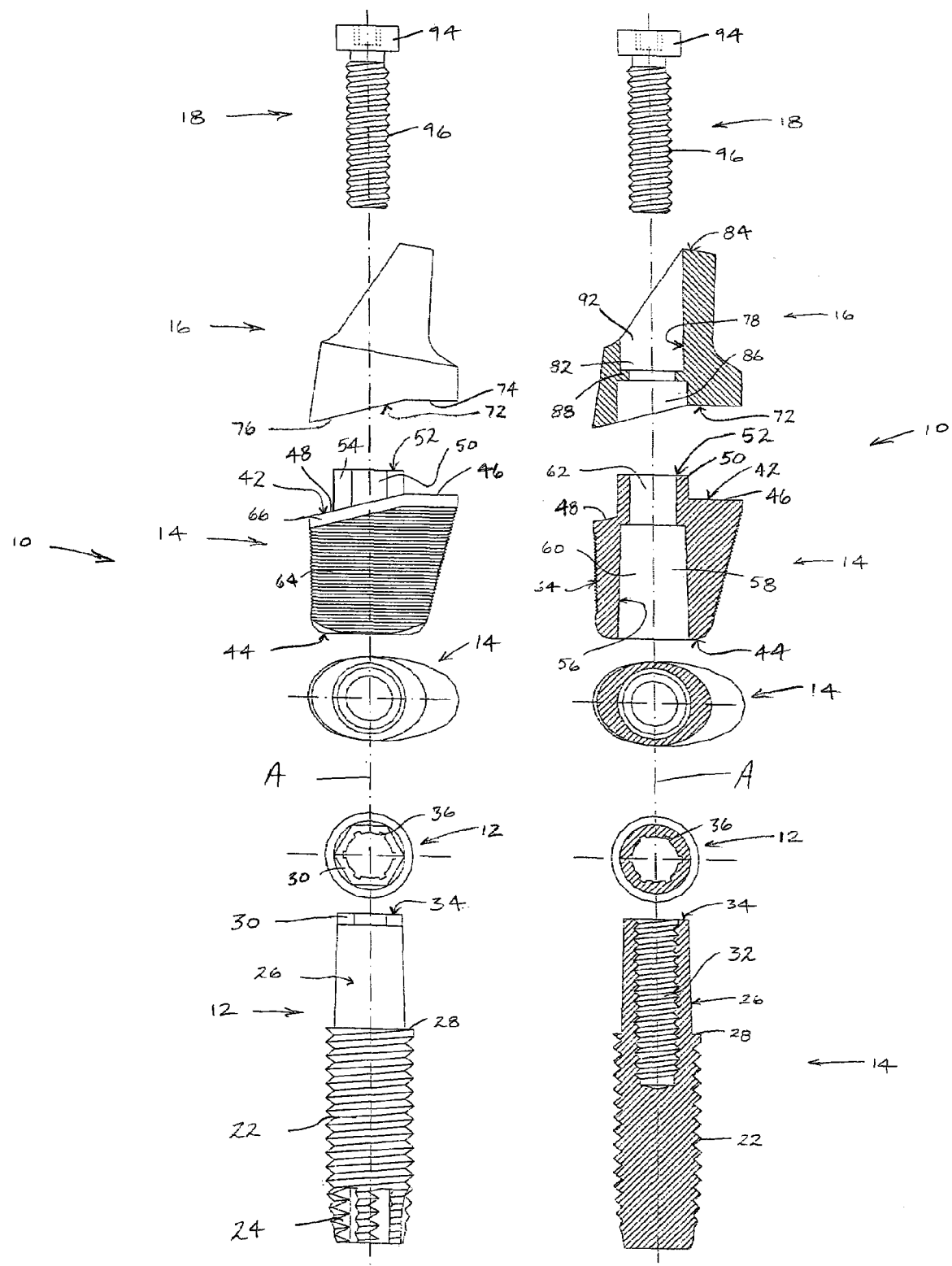
FIG. 5 is an exploded view of an embodiment of a dental implant assembly also including a top plan view of an apical insert of the assembly and a bottom plan view of a coronal base of the assembly.
FIG. 6 is an exploded, cross-sectional view of the assembly of FIG. 5.

Referring now to the drawings wherein the showings are for the purpose of illustrating the preferred embodiments only and not for the purpose of limiting same, FIGS. 5 and 6 illustrate one embodiment of a dental implant assembly 10. The dental implant assembly generally includes an apical insert 12, a coronal base 14, an abutment 16 and a fastener 18. FIG. 3 illustrates a portion of a jawbone having sockets SK left by removed teeth and an outline of the dental implant assembly 10 superimposed over the sockets. Each assembly can include one or more components that is at least partially noncircular and thus substantially fill a portion of each socket SK such that the gaps GP, as illustrated in FIG. 2, are significantly reduced or eliminated. Furthermore, dimensions B shown in FIG. 3 can be significantly greater than dimension A as illustrated in FIG. 2 when superimposed over the same section of jawbone. This is due to the noncircular shape of at least a portion of the one or more components of the assembly 10, which provides the added clearance between the assemblies. FIG. 4 illustrates a section of the anterior maxilla with an outline of dental implant assembly 10 superimposed over the cross section. The abutment 16 supports a prosthetic tooth or crown C.

With reference back to FIGS. 5 and 6, the apical insert 12 includes a plurality of external threads 22 that extend along a portion of the length of the insert. The external threads 22 terminate with one or more self-tapping threads 24 at a first end of the insert. These threads are used to facilitate in securing the apical insert in the jawbone. As can be appreciated, the apical insert can be absent external threads and/or self tapping threads; thus other or additional arrangements can be used to facilitate in securing the apical insert in the jawbone. The apical insert 12 also includes an external tapered surface 26 extending from the external threads 22 toward the top of the apical insert. In the depicted embodiment, tapered surface 26 is smooth, i.e. having no threads; however, the tapered surface can include one or more non-smooth regions (e.g., grooves, ribs, etc.). The tapered surface 26 and the external threads 22 meet at a radial shoulder 28.

The tapered surface terminates near the top of the apical insert at polygonal pilot 30. The polygonal pilot 30 can be similarly shaped to a conventional nut and can be dimensioned for receipt inside a mounting tool (not shown) that is used to insert the apical insert 12 into the socket. The polygonal pilot is shown to be hexagonal; however, it can be appreciated that the polygonal pilot can have other shapes (e.g., oval, 3-sides, 4-sides, 5-sides, etc.). As can be appreciated, the configuration of the polygonal pilot 30 can have many other or additional configurations if another mounting tool or another mounting technique is used.

As illustrated in FIG. 6, the apical insert includes threaded opening 32 which extends axially into the apical insert 12 from an end surface 34 located at a second (upper in FIG. 5) end of the insert through the portion of the insert defined by the tapered external surface 26 and into the portion defined by the external threads 22. Axial ridges 36 can be formed in at least a portion of the threaded opening 32; however, this is not required. The ridges 36 can receive a mounting tool (not shown) that is used to insert the apical insert 12 into the socket. Threaded opening 32 is designed to receive the threaded end of fastener 18 as described below. As can be appreciated, opening 32 can include other connection arrangements other than threads to engage the end of fastener 18, especially when the end of fastener 18 has a non-threaded end.

As discussed in U.S. patent application Ser. No. 10/216, 307, which is incorporated herein by reference, one or more interlocking features (not shown) can extend radially outwardly from and/or be formed on tapered surface 26. The interlocking features can limit rotational movement of the coronal base 14 with respect to the apical insert 12 when the coronal base is connected to the apical insert.

The coronal base 14 extends between an abutment mounting platform surface 42 and a bottom surface 44. In the depicted embodiment, the abutment mounting platform surface 42 includes a transverse portion 46, which is substantially normal to a longitudinal axis A of the assembly, and an angulated portion 48, which is at an angle other than normal to the longitudinal axis A of the assembly. The angle of the angulated portion 48 from horizontal, i.e. the plane in which the transverse portion 46 lies in FIG. 5, measures about 5 to about 60 degrees. As can be appreciated, the coronal base is not required to include a sloped platform surface. As can also be appreciated, the platform surface can have many other configurations. The non-flat platform surface facilitates in properly orienting and/or maintaining the abutment 16 in position on the coronal base. The shape of the abutment mounting platform surface 42 can take a number of other configurations, some of which will be described in more detail below with regard to other embodiments. Providing different embodiments having differently angled abutment mounting platform surfaces allows for providing different angulated abutments that more closely match the angulation of the jaw bone at the root level, as is the case with natural teeth. The angulated portion 48 of the abutment mounting platform surface 42 provides a better starting point, as opposed to known devices, in those cases where the axis of the implant and that of the crown are not aligned but at an angle. Such a configuration is especially useful in the anterior maxilla where the alveolar ridge usually is at an angle with the emerging crown. This configuration also improves the emergence profile and harmonizes the angulation between the alveolar ridge and the crown.

A pilot 50 extends from the abutment mounting platform surface 42 and terminates at a top surface 52. A plurality of flats 54, similar to a hexagonal nut, are provided along the pilot 50 to engage the abutment 16 and prevent relative rotation thereof. It will be appreciated, however, that such anti-rotation flats are optional. If provided, however, such flats may alternatively take any suitable form (e.g., 3-sides, 4-side, ribs, grooves, etc.) to inhibit or prevent rotation of the abutment relative to the coronal base.

The coronal base 14 also includes an inner surface 56 defining a mounting passage 58 extending between the top surface 52 of the pilot 50 and bottom surface 44. The inner surface 56 includes a tapered portion 60 and a generally cylindrical portion 62. The tapered portion is designed to mate with tapered surface 26 of the apical insert. As can be appreciated, the tapered portion can be generally smooth or non-smooth. A non-smooth tapered portion can be used to inhibit or prevent rotational movement of the coronal base relative to the apical surface; however, this is not required. As can also be appreciated, cylindrical portion 62 can have a non-circular cross-sectional shape. The cross-section of the cylindrical portion is sized and shaped to enable the lower portion of fastener 18 to pass through the cylindrical portion. As shown in FIG. 6, the passage length of the tapered portion is greater than the length of the cylindrical portion, and the maximum cross-sectional width of the tapered portion is greater than the maximum cross-section width of the tapered portion.

The coronal base 14 is supported on the apical insert 12 such that tapered portion 60 of inner surface 56 of the coronal base engages the external tapered surface 26 of the apical insert. Typically, tapered portion 60 of inner surface 56 of the coronal base will be dimensionally the same size or slightly smaller than the external tapered surface 26 of the apical insert such that the tapered portion 60 will frictionally engage the external tapered surface 26 to form a Morse fit thereby retaining the coronal base 14 on apical insert 12. Corresponding interlocking features (not shown) can be provided along inner surface 56 adjacent the bottom surface 44 to cooperate with the interlocking features of the apical insert 12 that were described above and are more particularly described in U.S. patent application Ser. No. 10/216, 307, which is incorporated herein by reference.

In the depicted embodiment, the lower portion of coronal base 14 has a non-circular cross-sectional shape; however, this is not required. In one non-limiting embodiment, the lower portion of coronal base 14 has a generally oval-shaped periphery. In other non-limiting embodiments, the lower portion of coronal base 14 can have a D-shaped or other non-circular periphery that more closely corresponds to the shape of the socket into which the apical insert 12 and base will be implanted. Accordingly, it will often be desirable to orient the coronal base 14 on the apical insert 12 relative to the surrounding teeth or other implants to better align the prosthetic tooth or crown therewith. The coronal base 14 can be installed in any one of multiple positions relative to the apical insert to better align the coronal base and associated abutment 16, and ultimately the prosthetic tooth or crown, with the adjacent teeth or implants. Typically when the coronal base is secured to the apical insert, at least a portion of the lower portion of the coronal base is positioned below the upper surface of the jaw bone; however, this is not required. When at least a portion of the lower portion of the coronal base is positioned below the upper surface of the jawbone, the bone on the jawbone will eventually grow back and facilitate in locking the coronal base on the apical insert and in position relative to the jawbone; thereby providing for a more stable and secure dental implant, and also forming a more natural looking and aesthetically pleasing dental implant.

The coronal base 14 includes an outer surface 64 that extends from the bottom surface 44 to a band 66 that is provided adjacent the abutment mounting platform surface 42. Typically, this outer surface 64 is etched, sand blasted, threaded, machined or otherwise roughened in such a way as to promote bone growth and/or osseointegration on the at least a portion of the outer surface of the coronal base, thereby facilitating in quick stabilization of the coronal base relative to the jawbone. As can be appreciated, the outer surface of the coronal base can be generally smooth. Band 66 is generally smooth and has a width dimension of about 0.25 to 5.00 mm and typically about 1 to 3 mm; however, other widths can be used. As can be appreciated, band 60 can include a non-smooth surface. Band 66 at least generally follows the contour of the mounting platform surface 42. The band 66 is typically left untreated to prevent microbiological contamination.

Abutment 16 is designed to accommodate a prosthetic tooth or crown C. Abutment 16 includes a lower surface 72 that complements the abutment mounting platform surface 42 when the abutment is mounted to coronal base 14. Accordingly, in the embodiment depicted in FIGS. 5 and 6, the lower surface 72 includes a transverse portion 74 that contacts the transverse portion 46 of the abutment mounting platform surface 42 and an angulated portion 76 that contacts the angulated portion 48 of the mounting surface 42.

Abutment 16 also includes an inner surface 78 defining a mounting passage 82 extending between a top surface 84 and the bottom surface 72. The mounting passage 82 includes a lower portion 86 defined below a radial shoulder 88 and an upper portion 92 defined above the radial shoulder. The radial shoulder 88 extends into the mounting passage 82 towards the longitudinal axis A. Lower portion 86 of the mounting passage 82 is dimensioned to receive pilot 50 of the coronal base 14. The lower portion 86 can be dimensioned to snugly receive the pilot 50, e.g. include flattened sections that cooperate with the flats 54 of the pilot. In such an embodiment, the abutment 16 will not rotate in relation to the coronal base 14, and vice versa. Alternatively, the lower portion 86 of the mounting passage 82 can be shaped to receive the pilot 50 while allowing for relative rotation of the abutment 16 and/or the base 14. The upper portion 92 of the mounting passage 82 accommodates a head 94 of the fastener 18. The radial shoulder prevents the head 94 of fastener 18 from moving into lower portion 86 of passage 82.

To fasten the system 10 together, the fastener 18 is inserted through mounting passages 58 and 82 such that a threaded shank 96 of the fastener can be received in the threaded passage 32 of the apical insert 12. The head 94 of the fastener 18 contacts the shoulder 88 in the abutment 16. The head of fastener 18 includes an opening to receive a tool, not shown, for securing the shank of the fastener to the apical insert. The size and cross-sectional shape of passages 58 and 82 are such that threaded shank 96 does not secure to the side walls of such passages; however, this is not required.

Figures 7, 8:
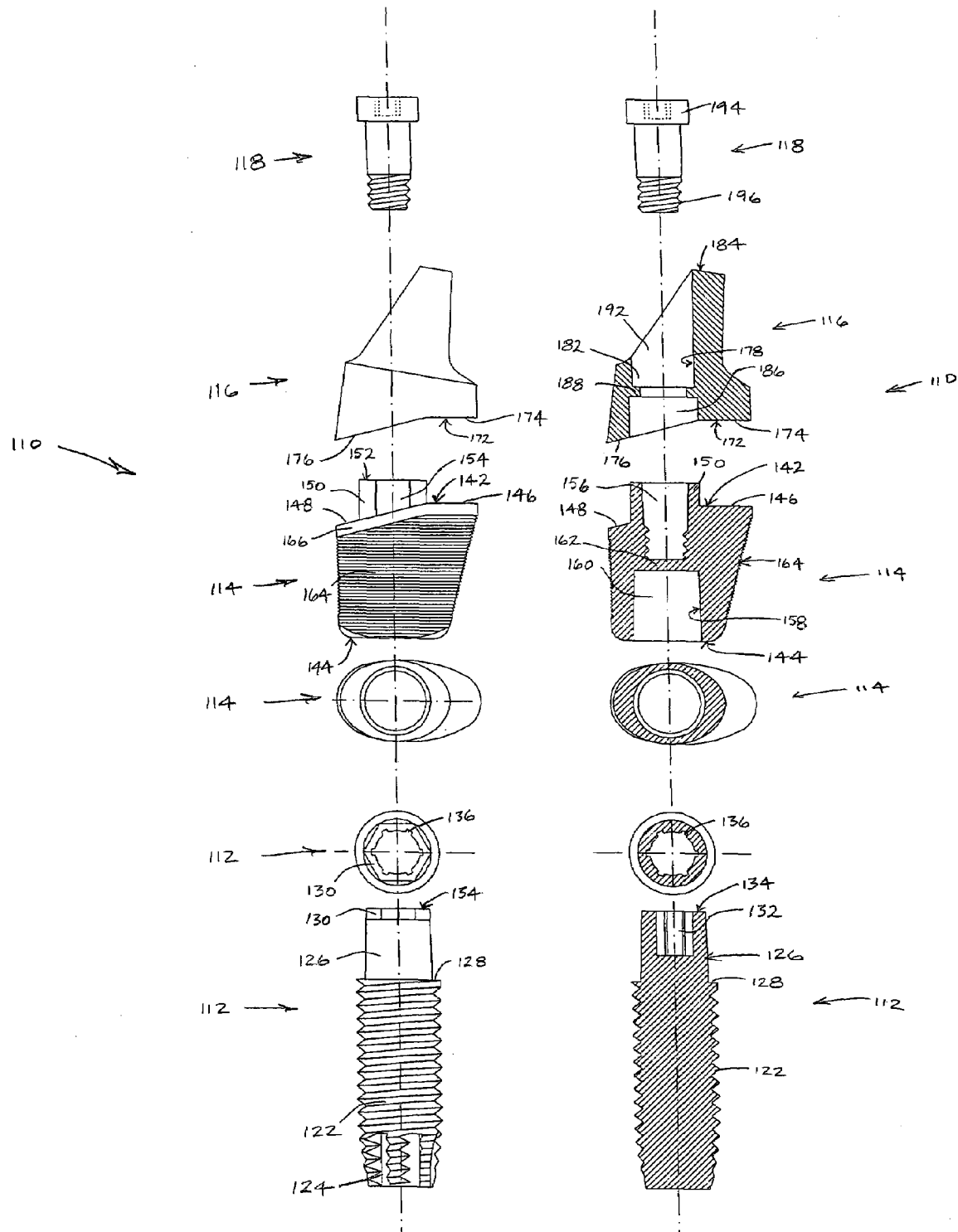
FIG. 7 is an exploded view of another embodiment of a dental implant assembly also including a top plan view of an apical insert of the assembly and a bottom plan view of a coronal base of the assembly.
FIG. 8 is an exploded, cross-sectional view of the assembly shown in FIG. 7.

Referring now to FIGS. 7 and 8, another embodiment of a dental implant assembly 110 is illustrated. The dental implant assembly includes an apical insert 112, a coronal base 114, an abutment 116 and a fastener 118. The dental implant assembly 110 depicted in FIGS. 7 and 8 is similar to the assembly 10 depicted in FIGS. 5 and 6 in that the assembly has a cross-sectional profile to at least substantially fill the socket from which the tooth was extracted. The assembly depicted in FIGS. 7 and 8, however, allows for a simpler connection between the coronal base 114 and the apical insert 112.

The apical insert 112 can have an exterior structure that is the same as or similar to the exterior structure of the apical insert of FIGS. 5 and 6 as set forth above. In addition, the apical insert can have a method of insertion into the jawbone that is the same or similar to the method of insertion of the apical insert of FIGS. 5 and 6 as set forth above. As shown in FIGS. 7 and 8, the apical insert includes a plurality of external threads 122 that extend along a portion of the length of the insert. The external threads 122 terminate with one or more self-tapping threads 124 at a first (lower in FIG. 7) end of the insert. The apical insert 112 also includes an external tapered surface 126 extending from the external threads 122 toward the coronal base 114, when the system 110 is finally assembled. In the depicted embodiment, the tapered surface 126 is smooth, i.e. having no threads; however, the tapered surface can include a surface that is not completely smooth. The tapered surface 126 and the external threads 122 meet at a radial shoulder 128.

A polygonal pilot 130 extends from the tapered surface 126 toward the coronal base 114, when the system 110 is finally assembled. The polygonal pilot 130 can be similarly shaped to a conventional nut and can be dimensioned for receipt inside a mounting tool (not shown) that is used to insert the apical insert 112 into the socket. The pilot 130 can take other configurations if another mounting tool or another mounting technique is used.

An opening 132 extends axially into the apical insert 112 from an end surface 134 located at a second (upper in FIG. 7) end of the insert into the portion of the insert defined by the tapered external surface 126. In contrast to the embodiment depicted in FIGS. 5 and 6, the opening 132 does not extend into the portion defined by the external threads 122; however, this is not required. Furthermore, the opening 132 is not threaded or designed to receive shank 196 of fastener 118. Axial ridges 136 can be formed in at least a portion of the opening 132; however, this is not required. The ridges 136 can receive a mounting tool (not shown) that is used to facilitate in the insertion of the apical insert 112 into the socket in the jawbone. The opening 132 can be adapted to receive an Allen wrench to tighten the insert into the patient's jaw bone. Using an Allen wrench, or other similar tool that is received inside the opening 132 to insert the apical insert 112, lessens any likelihood of damaging the tapered external surface 126.

As discussed in U.S. patent application Ser. No. 10/216,307, a plurality of interlocking features (not shown) can extend radially outwardly from the tapered surface 126. The interlocking features can limit rotational movement of the coronal base 114 with respect to the apical insert 112.

The coronal base 114 extends between an abutment mounting platform surface 142 and a bottom surface 144. The coronal base 114 can have an exterior structure that is the same as or similar to the exterior structure of the coronal base of FIGS. 5 and 6 as set forth above. In addition, the coronal base can have a method of insertion onto the apical insert that is similar to the method of insertion of coronal insert on the apical insert of FIGS. 5 and 6 as set forth above. In the embodiment depicted in FIGS. 7 and 8, the abutment mounting platform surface 142 on the coronal base 114 includes a transverse portion 146, which is substantially normal to a longitudinal axis A of the assembly, and an angulated portion 148, which is at an angle other than normal to the longitudinal axis A of the assembly. The angle of the angulated portion 148 from horizontal, i.e. the plane in which the transverse portion 146 lies in FIG. 7, measures about 5 to about 60 degrees. The shape of the abutment mounting platform surface 142 can take a number of other configurations, some of which will be described in more detail below with regard to other embodiments. Providing different embodiments having differently angled abutment mounting platform surfaces improves the performance of angulated abutments since the angulation of the abutment can more closely match that at the root level of the jawbone, as is the case with natural teeth. The angulated portion 148 of the abutment mounting platform surface 142 provides a better starting point, as opposed to known devices, in those cases where the axis of the implant and that of the crown are not aligned but at an angle. Such a configuration is especially useful in the anterior maxilla where the alveolar ridge usually is at an angle with the emerging crown. This configuration also improves the emergence profile and harmonizes the angulation between the alveolar ridge and the crown.

A pilot 150 extends from the abutment mounting platform surface 142 and terminates at a top surface 152. A plurality of flats 154 are provided along pilot 150 to engage the abutment 116 and prevent relative rotation thereof. It will be appreciated, however, that such anti-rotation flats are optional. If provided, however, such flats may take any suitable form to prevent rotation of the abutment relative to the coronal base.

The coronal base 114 includes a threaded passage 156 extending into the base from the top surface 152 of the pilot 150. This configuration is different from the configuration of the coronal base illustrated in FIGS. 5 and 6. The threaded passage 156 is designed to receive and secure to fastener 118 to attach the abutment 116 to the coronal base 114. The coronal base 114 also includes a lower inner tapered surface 158 that defines a tapered socket 160 that is adapted to receive the upper portion of the apical insert 112 defined by the tapered surface 126. The threaded passage 156 and the tapered socket 160 are aligned along the axis A and are separated from one another by an internal wall 162 that, in the depicted embodiment, is normal to the longitudinal axis A. As can be appreciated, the wall separating the threaded passage and tapered socket is not required.

The coronal base 114 is supported on the apical insert 112 such that the inner tapered surface 158 of the coronal base engages the external tapered surface 126 of the apical insert. Typically, the tapered socket 160 the coronal base will be dimensionally the same size or slightly smaller than the external tapered surface 126 of the apical insert such that the tapered portion 160 will frictionally engage the external tapered surface 216 to form a Morse fit thereby retaining the coronal base 114 on apical insert 112.

Corresponding interlocking features (not shown) can be provided along inner surface 158 adjacent the bottom surface 144 to cooperate with the interlocking features of the apical insert 12 that were described above and are more particularly described in U.S. patent application Ser. No. 10/216,307, which is incorporated herein by reference. The lower portion of coronal base 114 is non-circular; however this is not require. In one non-limiting embodiment, the coronal base 114 has a generally oval-shaped periphery. In other non-limiting embodiments, the coronal base 114 can have a D-shaped or other non-circular periphery that more closely corresponds to the shape of the socket into which the apical insert 112 and base will be implanted. Accordingly, it will often be desirable to orient the coronal base 114 on the apical insert 112 relative to the surrounding teeth or other implants to better align the prosthetic tooth or crown therewith. The coronal base 114 can be installed in any one of multiple positions relative to the apical insert to better align the coronal base and associated abutment 116, and ultimately the prosthetic tooth or crown, with the adjacent teeth or implants.

The coronal base 114 includes an outer surface 164 that extends from the bottom surface 144 to a band 166 that is provided adjacent the abutment mounting platform surface 142. Typically, this outer surface 164 is etched, sand blasted, threaded, machined or otherwise roughened in such a way as to promote bone growth and/or osseointegration on the at least a portion of the outer surface of the coronal base, thereby facilitating in quick stabilization of the coronal base relative to the jawbone. As can be appreciated, the outer surface of the coronal base can be generally smooth. The band 166 remains generally smooth and has a width dimension of about 0.25 to 5.00 mm and typically about 1 to 3 mm.

The abutment 116 is designed to accommodate a prosthetic tooth or crown C. The abutment 116 can have an interior and/or exterior structure that is the same as or similar to the interior and/or exterior structure of the abutment of FIGS. 5 and 6 as set forth above. In addition, the abutment can have a method of insertion onto the coronal base that is the same or similar to the method of insertion of abutment on the coronal base of FIGS. 5 and 6 as set forth above. The abutment 116 as shown in FIGS. 7 and 8 includes a lower surface 172 that complements the abutment mounting platform surface 142 when the abutment is mounted to the coronal base 114. Accordingly, in the embodiment depicted in FIGS. 7 and 8, the lower surface 172 includes a transverse portion 174 that contacts the transverse portion 146 of the abutment mounting platform surface 142 and an angulated portion 176 that contacts the angulated portion 148 of the mounting surface 42.

The abutment 116 also includes an inner surface 178 defining a mounting passage 182 extending between a top surface 184 and the bottom surface 172. The mounting passage 182 includes a lower portion 186 defined below a radial shoulder 188 and an upper portion 192 defined above the radial shoulder. The radial shoulder 188 extends into the mounting passage 182 towards the longitudinal axis A. The lower portion 186 of the mounting passage 182 is dimensioned to receive the pilot 150 of the coronal base 114. The lower portion 186 can be dimensioned to snugly receive the pilot 150, e.g. include flattened sections that cooperate with the flats 154 of the pilot. In such an embodiment, the abutment 116 will not rotate in relation to the coronal base 114, and vice versa. Alternatively, the lower portion 186 of the mounting passage 182 can be shaped to receive the pilot 150 while allowing for relative rotation of the abutment 116 and/or the base 114. The upper portion 192 of the mounting passage 182 accommodates a head 194 of the fastener 118.

To fasten the system 110 together, the fastener 118 is inserted through the mounting passage 182 such that a threaded portion 196 of the fastener can be received in the threaded passage 156 of the coronal base 114. The head 194 of the fastener 118 contacts the shoulder 188 in the abutment 116. The head of fastener 118 includes an opening to receive a tool, not shown, for securing the shank of the fastener to the apical insert. Prior to, or after, mounting the abutment 116 to the coronal base 114, the coronal base 114 can be fit over the apical insert 112. Since the tapered surfaces 158 and 126 are adapted to cooperate with one another to provide a Morse fit connection, a slight tap on the coronal base 114, or the abutment 116 if the abutment is already attached to the coronal base, results in a connection between the coronal base and the apical insert. Such a connection removes the need to provide a fastener that extends all the way through the coronal base, thus reducing the number of components of the system. The Morse fit between the apical insert and the coronal base is designed to secure these two components together. When the apical insert is embedded fully in the jawbone such that the top of the apical insert is positioned below the top surface of the jawbone, at least a portion of the coronal base is embedded in the jawbone when secured to the apical insert. during the healing of the jawbone, the bone grows about a portion of the coronal base. When the coronal base includes a non-smooth outer surface 164, the growing bone cooperates with the Morse fit to secure and maintain the coronal base on the apical insert.

Referring now to FIGS. 9 and 10, another embodiment of a dental implant assembly 210 is illustrated. The dental implant assembly includes an apical insert 212 and an abutment 216. The dental implant assembly 210 depicted in FIGS. 9 and 10 is similar to the assembly 10 depicted in FIGS. 5 and 6 and the assembly 110 depicted in FIGS. 7 and 8 in that the assembly 210 has a cross-sectional profile to at least substantially fill the socket from which the tooth was extracted. The assembly depicted in FIGS. 9 and 10, however, allows for a simpler connection between the abutment 216 and the apical insert 212 without the need for a fastener.

The apical insert 212 depicted in FIGS. 9 and 10 is similar to or the same as the apical insert 112 depicted in FIGS. 7 and 8; therefore, for the sake of brevity, the reference numerals used to describe the apical insert 212 in FIGS. 9 and 10 will be increased by 100 to refer to the same feature found in the apical insert 112 described with reference to FIGS. 7 and 8. In addition, the apical insert can have a method of insertion onto the apical insert that is similar to the method of insertion of coronal insert on the apical insert of FIGS. 5-8 as set forth above.

The abutment 216 in the embodiment depicted in FIGS. 9 and 10 is a unitary body that combines the abutment and the coronal base of the embodiments described above. Since the tapered surfaces 258 and 226 are adapted to cooperate with one another to provide a Morse fit connection, a slight tap on the abutment 216 results in a connection between the abutment and the apical insert. Such a connection removes the need to provide a fastener that extends all the way through the abutment thus reducing the number of components of the system. The Morse fit between the apical insert and the abutment is designed to secure these two components together. When the apical insert is embedded fully in the jawbone such that the top of the apical insert is positioned below the top surface of the jawbone, at least a portion of the abutment is embedded in the jawbone when secured to the apical insert. During the healing of the jawbone, the bone grows about a portion of the abutment. When the abutment includes a non-smooth outer surface 264, the growing bone cooperates with the Morse fit to secure and maintain the abutment on the apical insert. As such, after the biological osseointegration process is accomplished, the lower portion of abutment 216 is functionally connected to the patient's jawbone (see FIGS. 11 and 12 described below), thus removal of the fastener from the assembly lowers the cost of the assembly and provides an easier connection between the apical insert and abutment.

Abutment 216 includes a lower inner tapered surface 258 that defines a tapered socket 260 that is adapted to receive the upper portion of the apical insert 212 defined by the tapered surface 226. The abutment 216 also includes an outer surface 264 that extends from a bottom surface 244 to a band 266. Typically, this outer surface 264 is etched, sand blasted, threaded, machined or otherwise roughened in such a way as to promote bone growth, osseointegration and quick stabilization. The band 266 remains generally smooth and has a width dimension of about 0.25 to 5.00 mm and typically about 1 to 3 mm. The band 266 in the depicted embodiment is contoured, e.g. arcuate or scalloped, to more closely simulate the gingival pattern after osseointegration, the advantages of which will be described in more detail below. The outer surface of the abutment above the treated surface 264 can be smooth, similar to the abutments that have been described throughout the description. The band 266, and thus the intersection of the treated surface 264 and the smooth surface has a smooth contour in a cross section taken from a lingual to a labial direction.

As discussed above, to fasten the abutment 216 to the apical insert 212, the socket 260 receives the upper portion of the apical insert 212. Since the tapered surfaces 258 and 226 are adapted to cooperate with one another to provide a Morse fit connection, a slight tap on the abutment 216 results in a connection between the abutment and the apical insert. Such a connection removes the need to provide a fastener.

Figure 11:
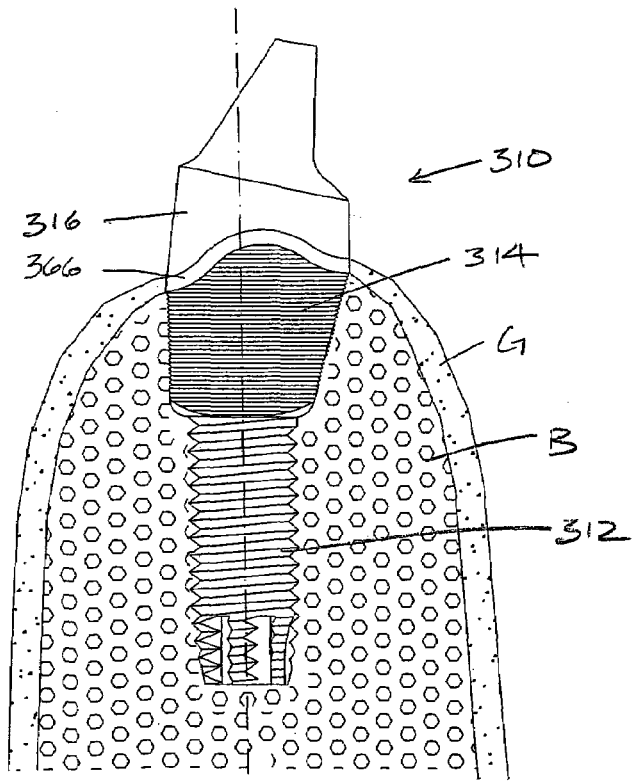
FIG. 11 is an assembled view of an embodiment of a dental implant assembly shown implanted into a patient's jawbone and gingival tissue after osseointegration, where the jawbone is shown in cross section taken from a lingual to a labial direction.
Figure 12:
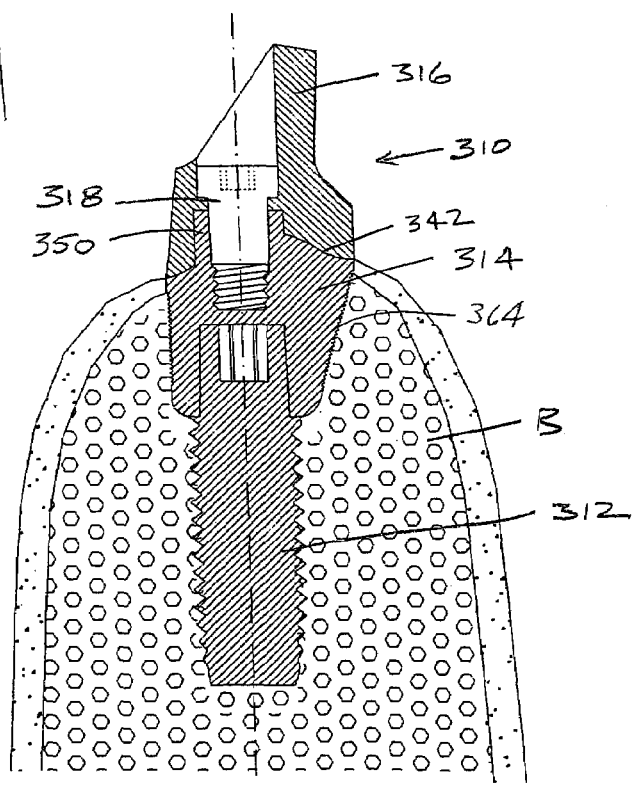
FIG. 12 is a cross-sectional view of the assembly shown in FIG. 11.

Referring now to FIGS. 11 and 12, there is depicted an assembly 310 after the biological osseointegration process, i.e. a functional connection between living bone and the surface of a load-carrying implant, is accomplished. The assembly 310 includes an apical insert 312, a coronal base 314, an abutment 316 and a fastener 318. The assembly depicted in FIGS. 11 and 12 is similar to the embodiment depicted in FIGS. 7 and 8, with the exception that an abutment mounting platform surface 342 for the coronal base 314, and a complementary contact surface 372 for the abutment 316 are scalloped, or arcuate. The scalloped profile can more closely resemble the emerging gingival profile. A bone B and gingival tissue G is shown in cross section in both FIGS. 11 and 12. The apical insert 312 is inserted into the bone B in a known manner.

As illustrated in FIGS. 11 and 12, the apical insert is inserted completely into the patient's jawbone B. The coronal base 314 is inserted to a depth such that after osseointegration a substantial portion of the coronal base is embedded in the patient's jawbone. Generally, at least about 5% percent of the coronal base is embedded in jawbone, typically at least about 10% percent of the coronal base is embedded in jawbone, more typically at least about 20% percent of the coronal base is embedded in jawbone, even more typically at least about 30% percent of the coronal base is embedded in jawbone, still more typically at least about 40% percent of the coronal base is embedded in jawbone, and still even more typically at least about 50% percent of the coronal base is embedded in jawbone.

As shown in FIGS. 11 and 12, when the bone B grows back, the top of the jawbone generally follows the contour of the band 366, which is left untreated. As more clearly seen in FIG. 12, over 50% the treated outer surface 364 is embedded in the patient's jawbone B after the bone has healed. For embodiments that include a pilot 350 (FIG. 12), the pilot 350 and the portion of the coronal base 314 defined by the band 366 are typically the only portion of the coronal base that is not embedded in the patient's jawbone. As illustrated in FIG. 12, over a majority of the coronal base is embedded in the patient's jawbone. Where the coronal base does not include a pilot, for example FIGS. 15 and 16, up to 95% or more of the volume of the coronal base can be embedded in the patient's jawbone.

Where the dental implant assembly is a two-piece system, for example the assembly depicted in FIGS. 9 and 10, the apical insert 212 is typically inserted completely into the patient's jawbone, similar to that shown in FIG. 12. The abutment 216 is inserted to a depth so that after the bone heals, the treated surface 264 is surrounded by bone, which is also similar to that shown in FIG. 12, except that the treated surface is found on the coronal base of the embodiment depicted in FIG. 12. The band 266 will be surrounded by gingival tissue and the remainder of the abutment will extend above the gingival tissue. Since the abutment 216 shown in FIGS. 9 and 10 is embedded in the bone after the bone has healed, there is no need for a fastener in this assembly.

With continued reference to FIGS. 11 and 12, after the bone has healed, the gingival tissue G grows at least partially around the band 366 of the coronal base 314. The smooth surface of the band inhibits the jawbone or tissue from securing to the band. The abutment 316 mounts to the coronal base 314 and is exposed above the patient's jawbone B and the gingival tissue G. Therefore, the scalloped configuration, or any configuration that more closely resembles the emerging gingival profile is desirable for aesthetic and hygienic reasons.

Figures 13, 14:
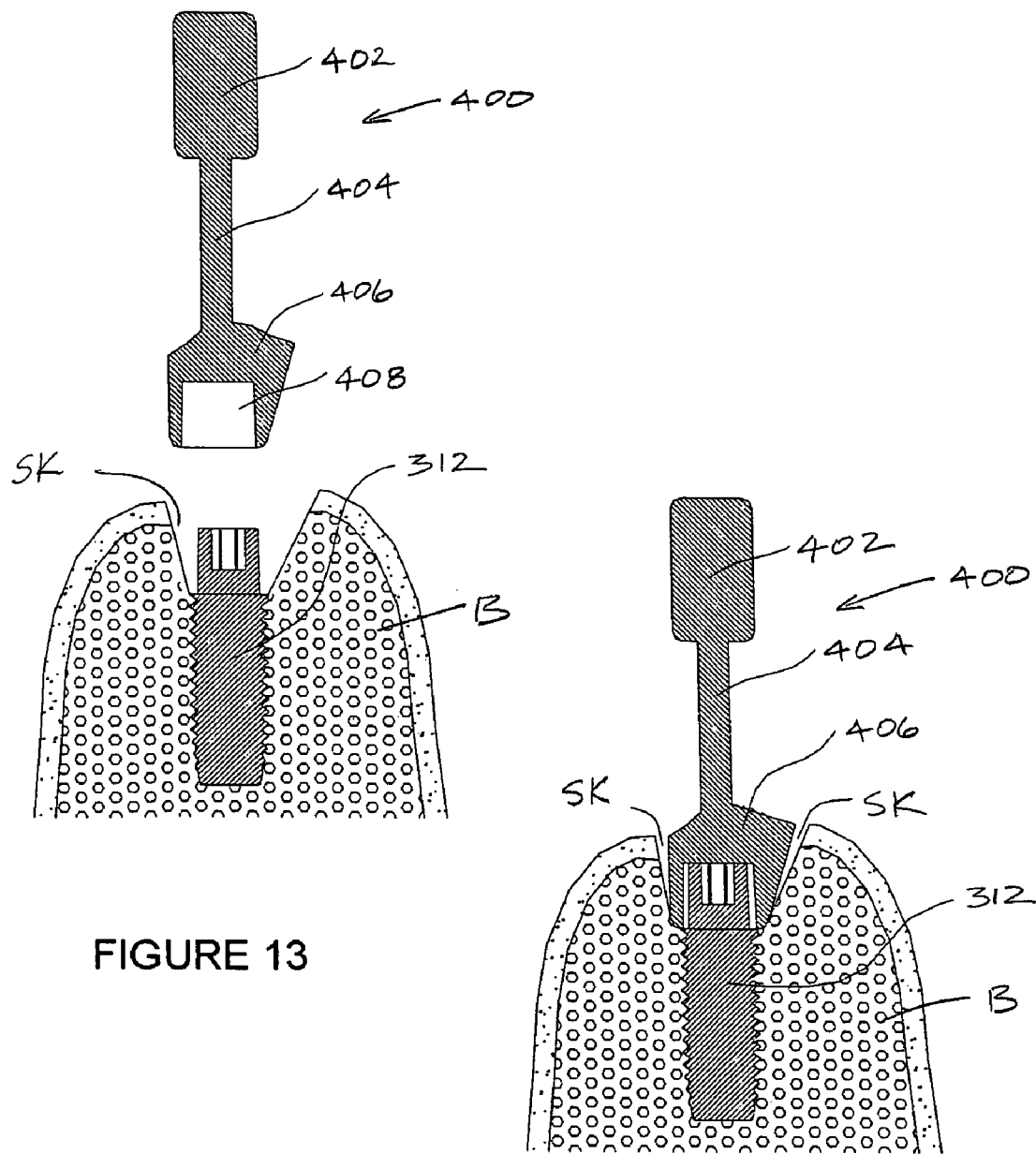
FIG. 13 is a cross-sectional view of an apical insert inserted into a patient's jawbone and a tool for use in measuring the distance that the apical insert is inserted into the patient's jawbone.
FIG. 14 is another view of the tool and apical insert shown in FIG. 13.

With reference to FIGS. 13 and 14, a tool 400 is used to determine a depth at which the apical insert 312 is to be driven. The tool 400 includes a handle 402, a shaft 404 that extends from the handle, and a lower body 406 connected to the shaft opposite the handle. The lower body 406 defines an interior cavity 408 having a larger radial dimension and the same axial dimension, as compared to the cavity 360 (FIG. 12) that receives the apical insert 312. The tool 400 is placed over the apical insert 312 in the socket SK from which the original tooth has been removed. The lower body 406 of the tool 400 has an upper surface that matches the contour of the abutment mounting platform surface 342 of the assembly 310. The apical insert 312 is driven to a depth so that after the bone B is healed, the contour of the abutment mounting platform surface 342 generally follows the contour of the healed bone. Accordingly, in alternative embodiments, the cavity 408 need not have an axial dimension that always corresponds to the cavity 360 (FIG. 12), if the upper surface of the tool aligns with the desired location for the abutment mounting platform or the desired location for the band and/or termination of the roughened surface.

Figure 15:
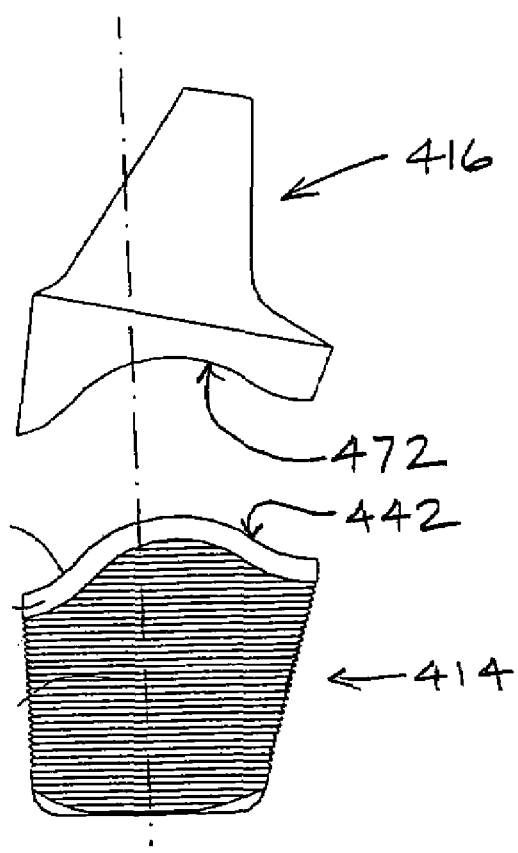
FIG. 15 is an exploded view of another embodiment of a dental implant assembly.
Figure 16:
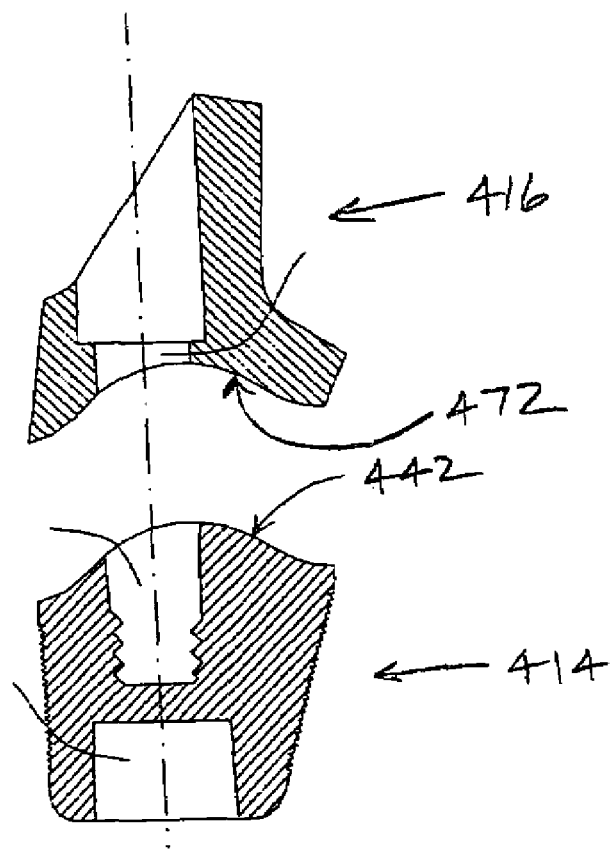
FIG. 16 is an exploded, cross-sectional view of the assembly shown in FIG. 15.

FIGS. 15 and 16 depict a coronal base 414 that does not include a pilot, such as that depicted in FIGS. 7 and 8. The coronal base 414 also includes a scalloped, e.g. contoured, platform abutment mounting surface 442 that more closely resembles the emerging gingival profile after osseointegration. An abutment 416 depicted in FIGS. 15 and 16 is similar to that depicted in FIGS. 7 and 8, except that includes a contact surface 472 that complements the shape of the platform abutment mounting surface 442.

Figure 17A:
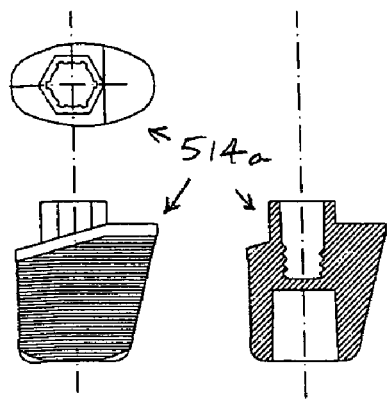
FIGS. 17A-17L each show a plan view, a side view, and a cross-sectional view of alternative embodiments of coronal bases.
Figure 17B:
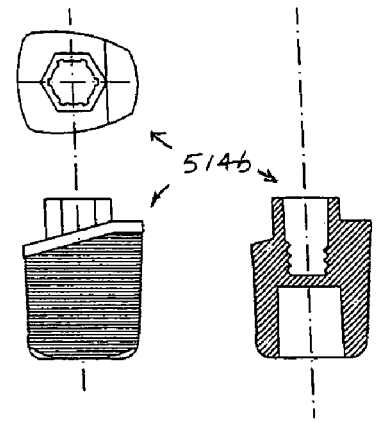
Figure 17C:
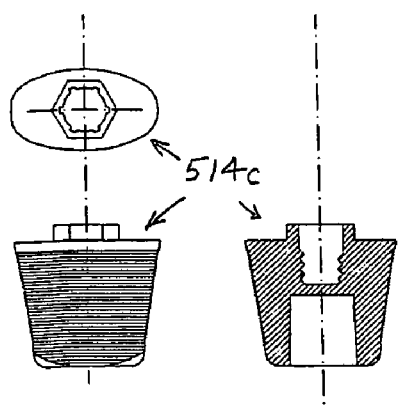
Figure 17D:
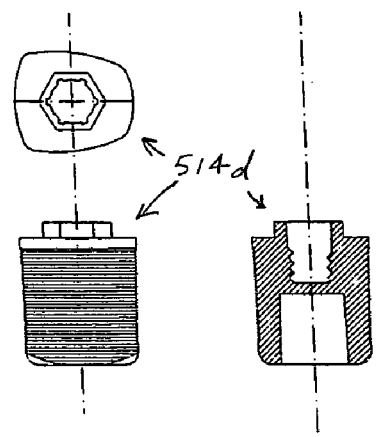
Figure 17E:
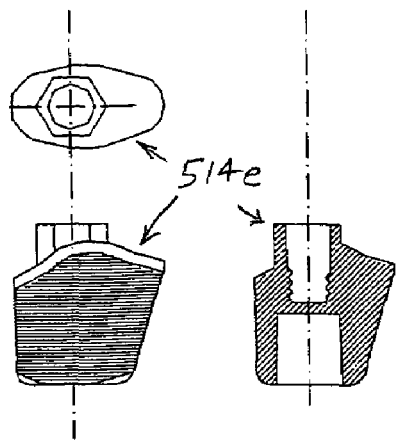
Figure 17F:
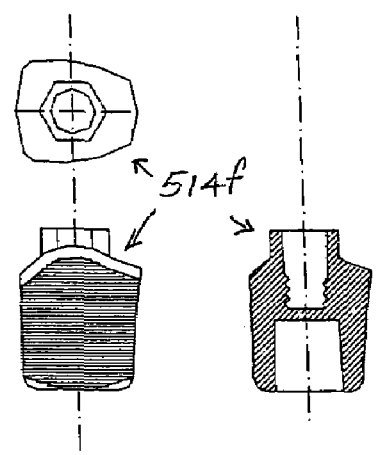
Figure 17G:
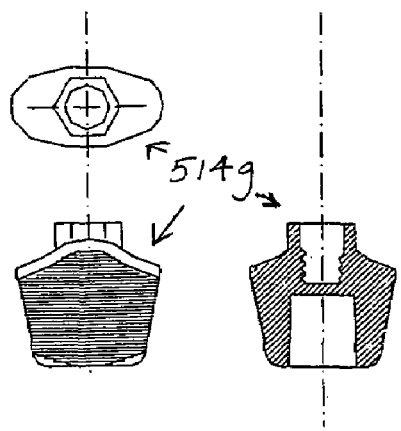
Figure 17H:
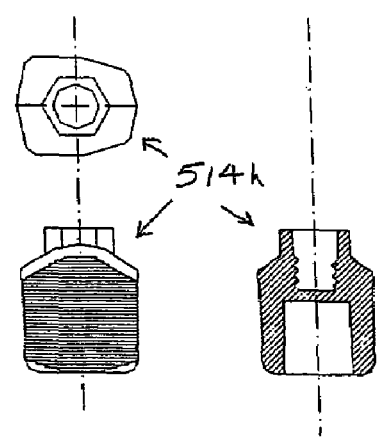
Figure 17I:
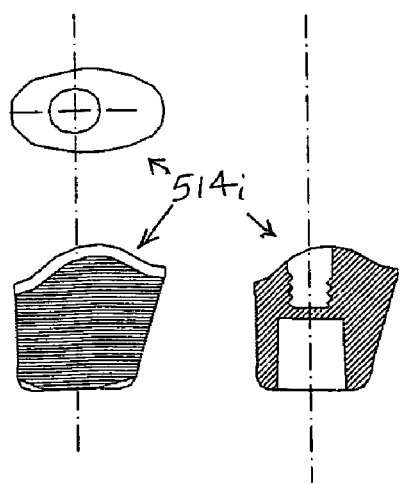
Figure 17J:
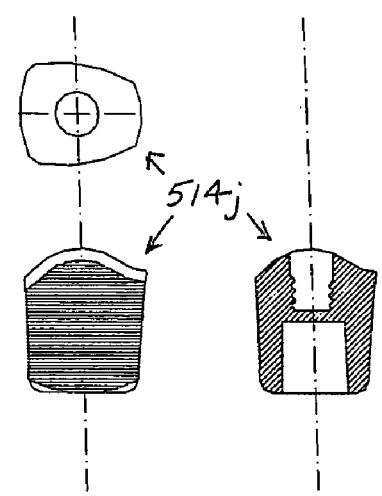
Figure 17K:
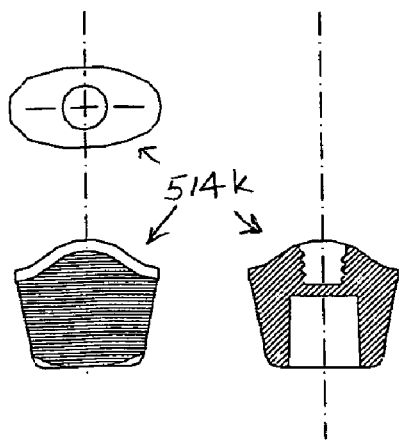
Figure 17L:
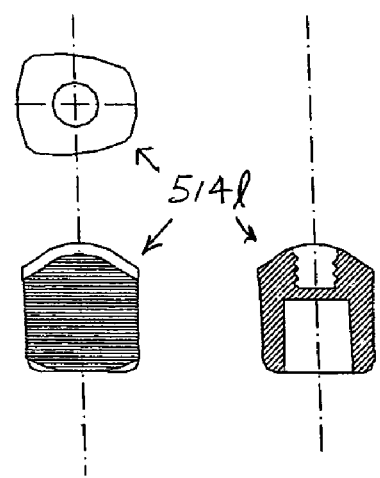

FIGS. 17A-17L depict different plan views and cross sections for a few of the many types of coronal bases that can be used in the present invention. The cross sections are taken where the labial side is depicted at the left and the lingual side is taken at the right for each figure. Coronal bases are depicted with a suffix that corresponds to the letter of the figure, for example 514a is shown in FIG. 17A. As seen in FIGS. 17A-17L, many different configurations are possible. For example, the coronal bases 514a, 514c, 514e, 514g, 514i and 514k that have a more oval-shape can be used for the anterior teeth. For example, the coronal bases 514b, 514d, 514f, 514h, 514j and 514l that have a more trapezoidal configuration can be used for the upper central incisor.

Figures 18A, 18B:
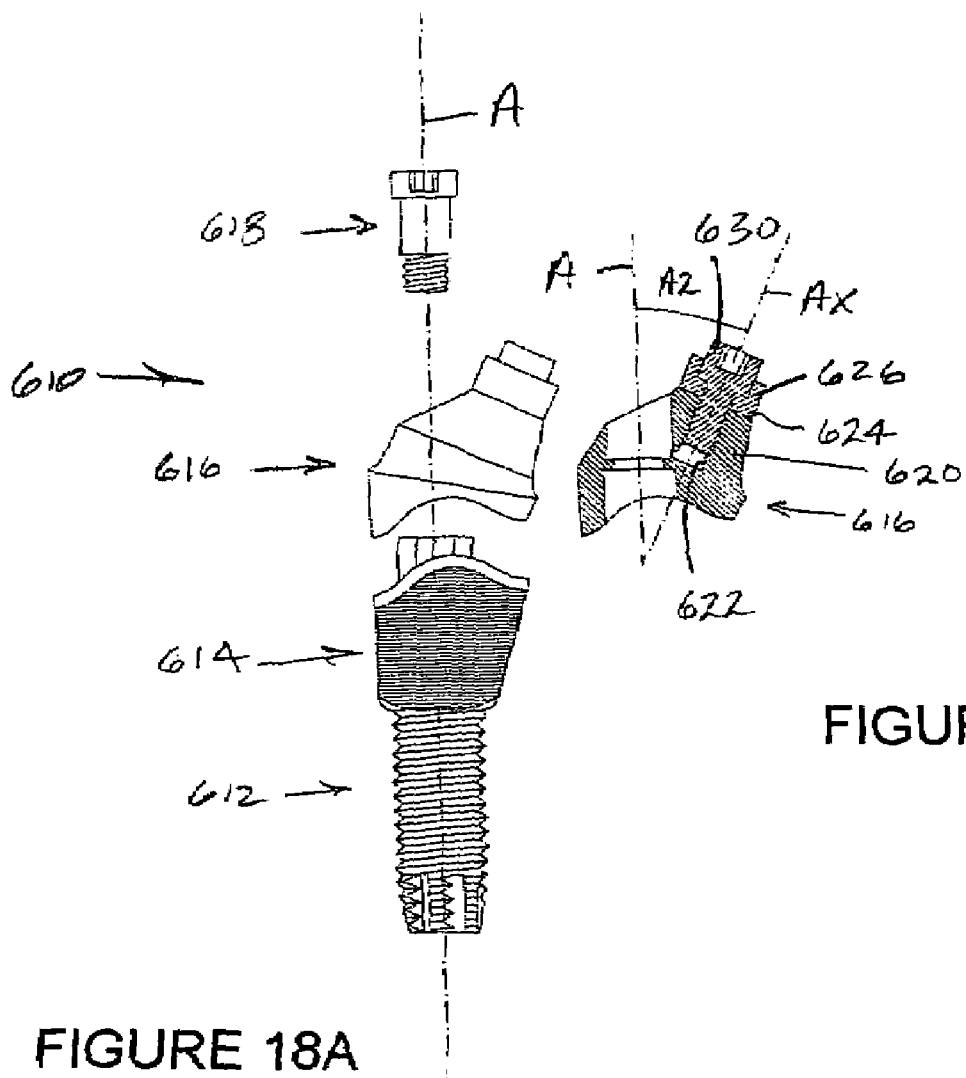
FIG. 18A is an exploded view of a dental implant assembly disclosing an alternative embodiment of an abutment.
FIG. 18B is a cross-sectional view of the abutment disclosed in FIG. 18.

FIGS. 18A and 18B depict an alternative abutment 616. This embodiment, though not strictly limited to this use, can be particularly useful when mounting to a coronal base 614 having an oval shaped configuration in plan view. The abutment 616 mounts to the coronal base 614 using a fastener 618. The coronal base 614 can mount to an apical insert 612 via a Morse fit, which is described above. The abutment 616 in this embodiment includes a projection 620 defining an axis AX. A threaded hole 622 extends into the projection along the axis AX from a projection end surface 624. The axis AX is disposed at an angle A2 from the longitudinal axis A of assembly 610. Generally, angle A2 is about 5 to 45 degrees, and typically about 15 to 35 degrees; however, other angles can be use. A collar 626 is supported on the abutment 616 at the end surface 624 and retained there by a fastener 630.

The angulated abutment depicted in FIGS. 18A and 18B provides a better starting point in those cases where the axis of the implant assembly and that of the crown, or prosthesis, are not aligned but at an angle. Such a configuration is especially useful in the anterior maxilla where the alveolar ridge usually is at an angle with the emerging crown. The depicted configuration also improves the emergence profile and harmonizes the angulation between the alveolar ridge and the crown.

FIGS. 19A, 19B, 20A and 20B respectively illustrate osteotomes 600 and 600' for use in surgically preparing the implantation site for receiving split implants in accordance with the present invention. Osteotome 600 includes a handle portion 602, a support post 604 and a blade 606. Osteotome 600' likewise includes a handle 602', a support post 604' extending from the handle and a blade 606'. Osteotomes 600 and 600' are different in that a blade can be used to provide a different profile to match that of the coronal base and/or abutment that will be inserted into the implantation site.

Figures 21A, 21B:
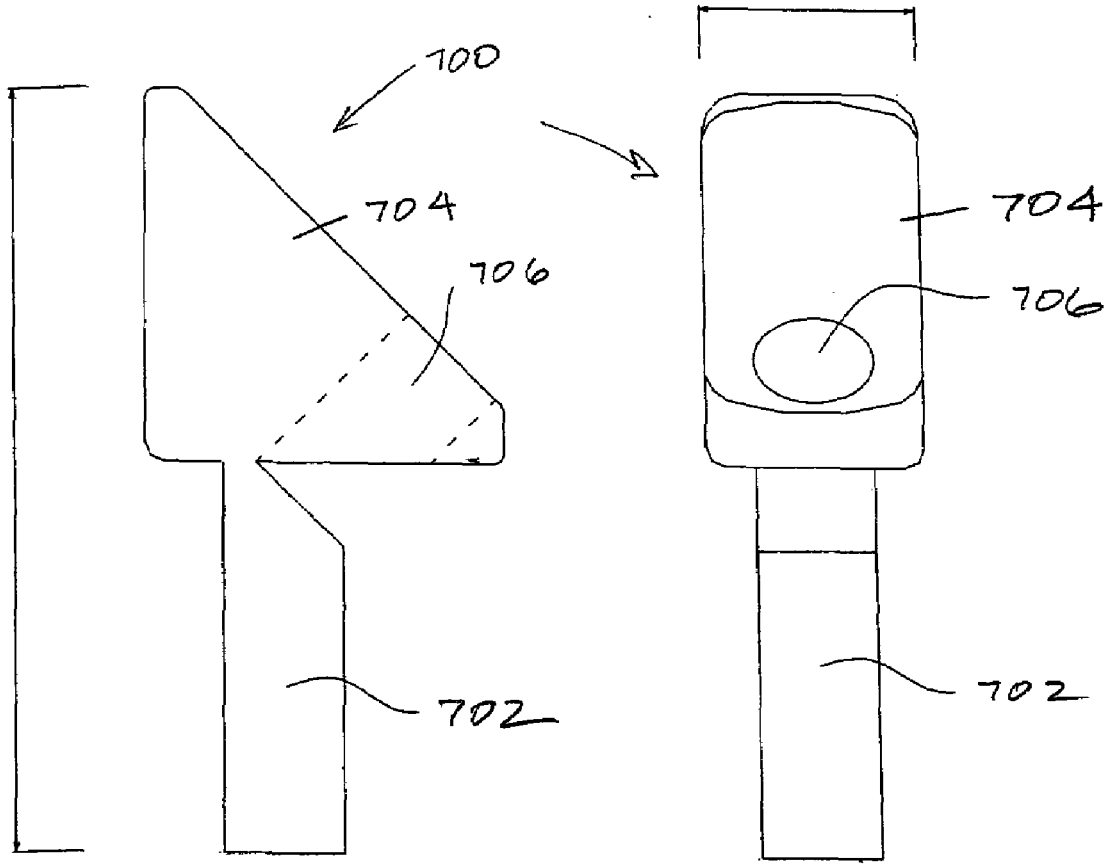
FIG. 21A is a first side view of a drill-guiding device for preparing an implantation site to receive a dental implant assembly.
FIG. 21B is a second side view of the drill-guiding device of FIG. 21A.
Figure 22:
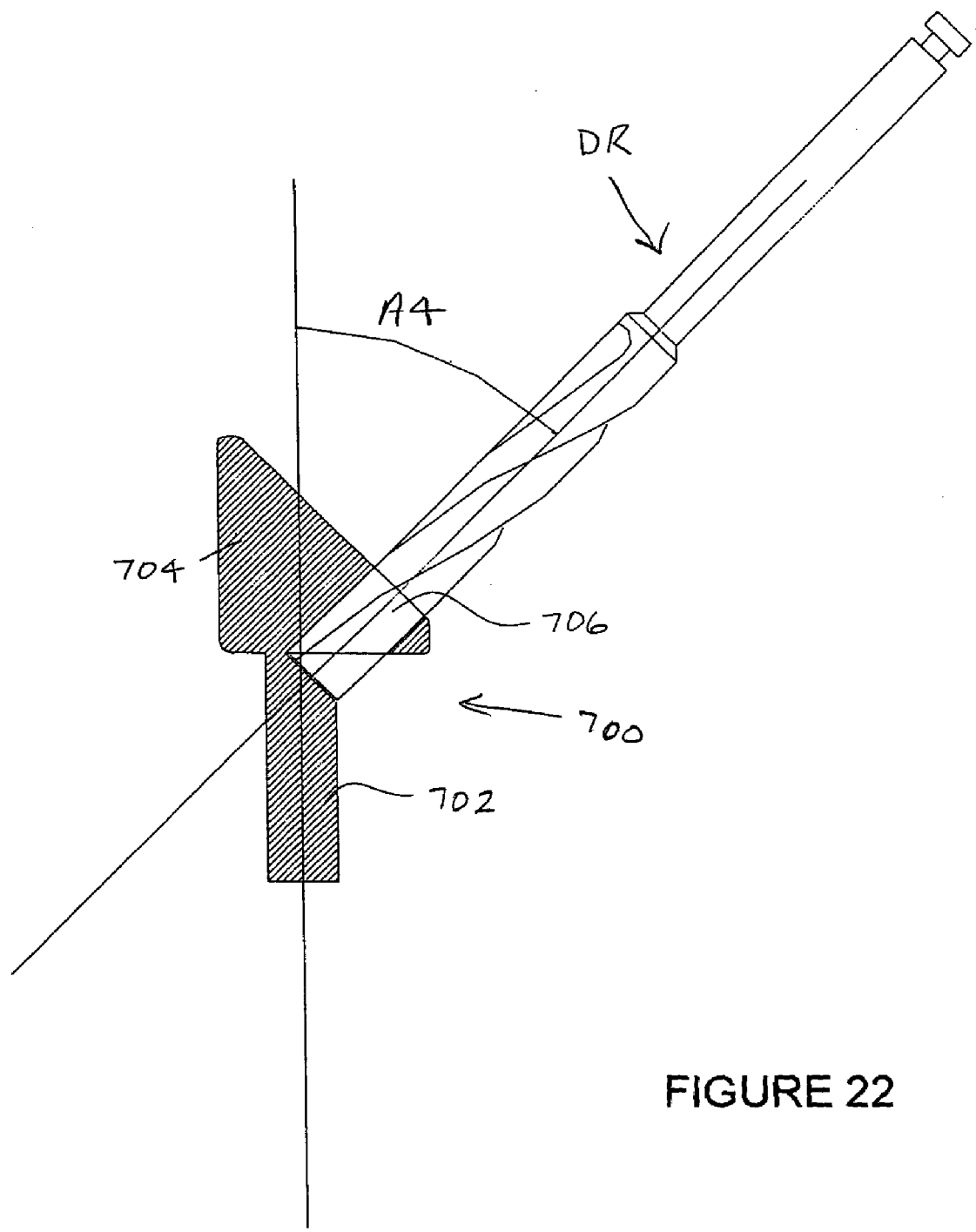
FIG. 22 is a cross-sectional view of the drill-guiding device of FIGS. 21A and B and a drill bit.

In certain situations, it may be necessary to set the split implant assembly at a site where a presence of cortical bone does not permit the use of an osteotome, such as those illustrated in FIGS. 19A, 19B, 20A and 20B. In such situations, a drill guide 700 and drill bit DR, shown in FIGS. 21A, 21B and 22, may be used to prepare the cavity or site for implantation of an assembly in accordance with the present invention. The drill guide 700 includes a support post 702 and a guide block 704 having a hole 706 projecting therethrough. As is better shown in FIG. 22, the support post 702 defines a centerline CL. Hole 706 is shown disposed relative to centerline CL at an angle A4. Generally, angle A4 is about 30 to 60 degrees and typically about 45 degrees; however, other angles can be used. In use, the support post 702 is inserted into a corresponding hole in the perforated bone. The drill guide together with the rotating drill is slid toward the implantation site until the desired size opening has been made. Once one side has been cut, the guiding tool and the drill are rotated 180 degrees to create the other side of the cavity or site.

The invention has been described with reference to the preferred embodiments. Modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method for inserting a dental implant assembly into a patient's jawbone, the method comprising:
   inserting an apical insert fully into a patient's jawbone such that a top surface of said apical insert is positioned below a top surface of said jawbone, said apical insert comprising a top and a bottom portion;
   mounting a coronal base to said top portion of said apical insert via a Morse taper fit without using a threaded engagement such that at least a portion of said component is positioned below a top surface of said jawbone; and fastening an abutment to said coronal base.

2. The method as defined in claim 1, further comprising positioning a tool over said apical insert to determine a depth at which said apical insert is to be inserted in said jawbone, said tool comprising a body defining an interior cavity having a larger radial dimension than said apical insert and an axial dimension such that a selected portion of the body aligns with a desired location for a lower portion of said coronal base.

3. The method as defined in claim 1, wherein said coronal base has an upper cavity, and fastening the abutment to said coronal base further comprising fastening the abutment via inserting a fastener through a mounting passage in said abutment and securing said fastener into said upper cavity of said coronal base.

4. The method as defined in claim 3, wherein said coronal base includes an internal lower wall that defines a lower surface of the opening.

5. The method as defined in claim 1, wherein said component includes a peripheral surface having a non-smooth portion to promote osseointegration, said non-smooth surface being defined by an upper limit that terminates in a profile that generally matches an emerging gingival profile of the patient after said jawbone is substantially healed.

6. The method as defined in claim 1, wherein said apical insert is inserted to a depth in the jawbone such that said apical insert is disposed completely within the jawbone and at least about 5% of said coronal base is disposed within the jawbone after the jawbone has healed.

7. The method as defined in claim 6, wherein at least about 10% of said coronal base is disposed within the jawbone after the jawbone has healed.

8. The method as defined in claim 7, wherein at least about 50% of said coronal base is disposed within the jawbone after the jawbone has healed.

9. A dental implant assembly comprising:
an apical insert designed to be inserted into an associated jawbone, said apical insert including a top and bottom portion, said bottom portion designed to engage the jawbone, said top portion including a tapered smooth surface terminating at a top end of said apical insert;
a coronal base including a first cavity and a second cavity and a peripheral surface having a roughened portion to promote osseointegration, said second cavity being dimensioned to receive a top portion of the apical insert such that the coronal base can mount to the apical insert substantially completely via a tapered Morse fit;
an abutment having a mounting passage; and,
a fastener designed to extend through the mounting passage of the abutment and engage and terminate in the first cavity of said coronal base, said fastener adapted to secure said abutment to said coronal base.

10. The assembly as defined in claim 9, wherein said apical insert includes a cavity configured for receiving an associated tool for inserting said apical insert into the associated jawbone, said cavity being configured to enable said apical insert to be rotatably inserted into the jawbone.

11. The assembly as defined in claim 10, wherein said cavity of the apical insert is designed to receive an Allen wrench.

12. The assembly as defined in claim 9, wherein said first cavity of the coronal base terminates at a wall that separates the first cavity from the second cavity.

13. The assembly as defined in claim 12, wherein the wall is at least substantially normal to a longitudinal axis of the coronal base.

14. The assembly as defined in claim 9, wherein the fastener terminates in the coronal base when the fastener attaches said abutment to the coronal base.

15. The assembly as defined in claim 9, wherein said coronal base includes a pilot that extends towards the abutment.

16. The assembly as defined in claim 15, wherein said mounting passage in said abutment is dimensioned to receive said pilot.

17. The assembly as defined in claim 9, wherein said coronal base includes a non-planar abutment mounting platform surface and said abutment includes a complementarily shaped contact surface that contacts said abutment mounting platform surface.

18. The assembly as defined in claim 17, wherein said abutment mounting platform surface has a smooth contour in a cross section taken from a lingual to a labial direction.

19. The assembly as defined in claim 9, wherein said coronal base includes a band on the peripheral surface adjacent the abutment mounting platform surface to inhibit osseointegration.

20. A method for inserting a dental implant assembly into a patient's jawbone, the method comprising:
inserting an apical insert into a patient's jawbone, said apical insert comprising a top and a bottom portion;
mounting a component to said top portion of said apical insert such that at least about 5% of said component is positioned below a top surface of said jawbone, said component including a peripheral surface having a non-smooth portion to promote osseointegration.

21. The method of claim 20, wherein said component includes an abutment mounting platform surface, the method further comprising attaching an abutment to said component wherein said component includes a complementarily shaped contact surface that contacts said abutment mounting platform surface.

22. The method of claim 21, wherein said component includes a threaded opening, wherein attaching said abutment further comprises inserting a threaded fastener through an opening in said abutment and threading said fastener into said threaded opening.

23. The method of claim 20, wherein mounting said component further comprises tapping said component onto said apical insert such that at least about 25% of said component is positioned below a top surface of said jawbone.

24. The method of claim 20, wherein mounting said component further comprises tapping said component onto said apical insert such that at least about 50% of said component is positioned below a top surface of said jawbone.

25. The method of claim 20, further comprising at least partially attaching said component to said apical insert via osseointegration.

26. The method of claim 25, wherein said apical insert is inserted into the patient's jawbone such that a top surface of said apical insert is positioned below a top surface of said jawbone.

* * * * *